(12) United States Patent
Brady et al.

(10) Patent No.: US 12,220,468 B1
(45) Date of Patent: *Feb. 11, 2025

(54) ATOMIC SCALE TOPICAL COMPOSITION WITH ENHANCED INTERSTITIAL CELLULAR UPTAKE FOR INCREASED MOISTURIZING, FLUIDITY, ANTIOXIDANT AND RADIATION PROTECTION, ANTIMICROBIAL CLEANSING AND THERAPEUTICS FOR OPTIMAL DERMAL INTEGRITY AND HOMEOSTASIS

(71) Applicants: Terry Earl Brady, The Valley (AI); Anthony Lee Dellinger, Burlington, NC (US); Lowell Hughes, The Valley (AI); Lori Bush, Sonoma, CA (US); Melinda K. M. Goddard, The Valley (AI); Abed Alqader Ibrahim, Greensboro, NC (US)

(72) Inventors: Terry Earl Brady, The Valley (AI); Anthony Lee Dellinger, Burlington, NC (US); Lowell Hughes, The Valley (AI); Lori Bush, Sonoma, CA (US); Melinda K. M. Goddard, The Valley (AI); Abed Alqader Ibrahim, Greensboro, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 18/636,721

(22) Filed: Apr. 16, 2024

Related U.S. Application Data

(63) Continuation-in-part of application No. 18/232,877, filed on Aug. 11, 2023, now Pat. No. 12,005,132.

(51) Int. Cl.
*A61K 8/02* (2006.01)
*A61K 8/19* (2006.01)
(Continued)

(52) U.S. Cl.
CPC ............... *A61K 8/025* (2013.01); *A61K 8/27* (2013.01); *A61Q 17/005* (2013.01); *A61Q 17/04* (2013.01);
(Continued)

(58) Field of Classification Search
None
See application file for complete search history.

(56) References Cited

U.S. PATENT DOCUMENTS

| 5,484,597 A | 1/1996 | Slavtcheff |
| 5,587,168 A | 12/1996 | Vanonou |

(Continued)

OTHER PUBLICATIONS

LibreTexts. "13.5.4: Fullerene Complexes." https://chem.libretexts.org/@go/page/391845 accessed on Jul. 30, 2024, pp. 13.5.4.1 through 13.5.4., 2 printed pages (Year: 2024).*

(Continued)

*Primary Examiner* — Isaac Shomer

(57) ABSTRACT

This invention proposes a multifunctional topical composition that integrates halogen-functionalized fullerenes (halofullerenes and halo-endofullerenes) and metallic nanoparticles (NPs) to provide comprehensive skin protection and sanitizing, cosmetic enhancement and in some embodiments, treatment for various conditions. Leveraging the atomic scale and physical characteristics of halogenated fullerenes for deeper tissue penetration, the composition can provide antioxidant, antimicrobial, and UV protective benefits to foster cellular integrity, proliferation, and differentiation as healthy tissue. The proposed formulation can penetrate the stratum corneum and diffuse into underlying skin layers due to atomic-scale NPs that can readily deliver active ingredients through the skin via the pores of sweat glands; the lipid matrix of the stratum corneum; and hair follicles, sebaceous glands, and pilosebaceous pores. This composition uses stable inorganic antibacterial agents with (Continued)

a robust safety profile. Furthermore, it can provide UV protection from harmful radiation. The formulation comprises active ingredients that are specific, safe, stable and effective—and can be produced economically, making it suitable for a broad range of skin protection, sanitizing, enhancement and therapeutic products that promote skin health and wellbeing.

10 Claims, 4 Drawing Sheets

(51) Int. Cl.
    *A61K 8/27*     (2006.01)
    *A61Q 17/00*     (2006.01)
    *A61Q 17/04*     (2006.01)
    *A61Q 19/08*     (2006.01)
    *C01B 32/152*     (2017.01)
    *C01G 5/00*     (2006.01)

(52) U.S. Cl.
    CPC ............... *A61Q 19/08* (2013.01); *A61K 8/19* (2013.01); *C01B 32/152* (2017.08); *C01G 5/00* (2013.01)

(56) References Cited

U.S. PATENT DOCUMENTS

| | | | |
|---|---|---|---|
| 5,932,251 | A | 8/1999 | Kirkpatrick |
| 6,720,006 | B2 | 4/2004 | Hanke |
| 10,934,168 | B1 * | 3/2021 | Brady .................. D06M 16/00 |
| 12,005,077 | B1 * | 6/2024 | Brady .................... A61K 33/38 |
| 12,005,132 | B1 * | 6/2024 | Brady ...................... A61K 8/27 |

OTHER PUBLICATIONS

Alan L. Balch and Krzysztof Winkler. "Electrochemistry of fullerene/transition metal complexes: Three decades of progress." Coordination Chemistry Reviews, vol. 438, 2021, Article 213623, pp. 1-71. (Year: 2021).*

Tse-Lok Ho. "The Hard Soft Acids Bases (HSAB) Principle and Organic Chemistry." Chemical Reviews, vol. 75, No. 1, Feb. 1975, pp. 1-20. (Year: 1975).*

Qin Chen and Jon Zubieta. "Coordination chemistry of soluble metal oxides of molybdenum and vanadium." Coordination Chemistry Reviews, 114 (1992) 107-167. (Year: 1992).*

Hong-Yan Shi, Bin Deng, Sheng-Liang Zhong, Lei Wanga and An-Wu Xu. "Synthesis of zinc oxide nanoparticles with strong, tunable and stable visible light emission by solid-state transformation of Zn(II)-organic coordination polymers." Journal of Materials Chemistry, vol. 21, 2011, pp. 12309-12315. (Year: 2011).*

Hana Stepankova et al. "The Anti-Proliferative Activity of Coordination Compound-Based ZnO Nanoparticles as a Promising Agent Against Triple Negative Breast Cancer Cells." International Journal of Nanomedicine, vol. 16, 2021, pp. 4431-4449 and S1-S24. (Year: 2021).*

Zhihong Yang and Changsheng Xie. "Zn2+ release from zinc and zinc oxide particles in simulated uterine solution." Colloids and Surfaces B: Biointerfaces 47 (2006) pp. 140-145. (Year: 2006).*

Alan L. Balch and Krzysztof Winkler. "Electrochemistry of fullerene/transition metal complexes: Three decades of progress." Coordination Chemistry Reviews 438 (2021) 213623, pp. 1-71. (Year: 2021).*

Lakshmy Ramachandran and Cherupally Krishnan Krishnan Nair. "Therapeutic Potentials of Silver Nanoparticle Complex of α-Lipoic Acid." Nanomaterials and Nanotechnology, vol. 1, No. 2, 2011, pp. 17-24. (Year: 2011).*

\* cited by examiner

ATOMIC SCALE TOPICAL COMPOSITION WITH ENHANCED INTERSTITIAL CELLULAR UPTAKE FOR INCREASED MOISTURIZING, FLUIDITY, ANTIOXIDANT AND RADIATION PROTECTION, ANTIMICROBIAL CLEANSING AND THERAPEUTICS FOR OPTIMAL DERMAL INTEGRITY AND HOMEOSTASIS

FIELD OF THE INVENTION

The present invention relates to a topical composition comprising incompressible nanoparticles such as halogenated, functionalized fullerenes and endohedral fullerenes with enhanced near surface epidermal (stratum corneum) absorption and adjacent surface cellular uptake (stratum lucidum, stratum granulosum, stratum spinosum, and stratum basale). The composition confers broad-spectrum antimicrobial and antioxidant activity to the applied region, reducing pathogen burden, scavenging reactive oxygen species (ROS), and promoting cellular regeneration. In another embodiment of the present invention, functional fullerene nanoparticles (NPs) are further engineered to protect the skin from UVA rays (UVA-2, 320-340 nm and UVA-1, 340-400 nm) that can cause free radical production and oxidative stress characterized by photoaging, wrinkles, elasticity loss and pigmentation changes, as well as DNA damage that can lead to oncogenesis. In yet other embodiments of the present invention, it is useful as an "alcohol-free sanitizer" and as a topical therapeutic composition, such as an antiseptic and healing agent in wound management.

BACKGROUND OF THE INVENTION

Human skin serves as a protective barrier against toxins and pathogens, although its effectiveness may vary based on the density of hair and hair follicles and changes in hormonal makeup. UV light exposure, genetics, nutrition and other environmental factors also influence epidermal integrity.

Microbiota, sebaceous gland activity and various cleansing routines can likewise affect the respective layers of the skin. Soaps and other surfactant cleansers can similarly remove protective lipid barriers and increase susceptibility to chemical and pathogenic irritants. In addition to perceived image enhancement, the skincare industry has increased consumer awareness and demand for skin hygiene and hydration products. However, the efficacy of such products in reaching deep skin layers is limited, and their use can contribute to the accumulation of microbial matter and inflammation. That said, dermal application of skincare products can nonetheless be more effective than systemic antibiotics to minimize pathogen colonization and maintain healthy skin and sebaceous glands.

Solar ultraviolet (UV) radiation can profoundly impact human skin. Stratospheric molecular oxygen in the atmosphere absorbs wavelengths below 242 nm (UVC 100-290 nm), leading to ozone production. UVB rays, within the 290-320 nm range, are partially absorbed by the resultant stratospheric ozone. However, UVA rays (UVA-2, 320-340 nm, and UVA-1, 340-400 nm) primarily drive metabolic reactions affecting human skin. The effects of UV radiation can be categorized based on exposure intensity. High dosage UVB radiation induces short-term reactions that lead to cholecalciferol (Vitamin D) synthesis and erythema. Conversely, prolonged exposure can prompt severe degenerative skin changes, such as skin cancer from epidermal cells and actinic keratosis formation. Additionally, UVA stimulates the production of reactive oxygen species (ROS), which subsequently activate matrix metalloproteinases, causing damage to collagen and other proteins—an integral part of the photoaging process. Effective sunscreens should thus shield the skin from both UVA and UVB radiation. Various NPs have been employed for radiation blockage, offering broad-spectrum protection, limited skin penetration, and non-inflammatory ingredients.

Ultraviolet shielding agents employed in topical consumer products fall into two main categories. The first includes UV-scattering agents, such as NPs of titanium dioxide and zinc oxide. The second comprises ultraviolet absorbers, incorporating organic compounds like benzophenone (Oxybenzone) and Butyl Methoxydibenzoylmethane (Avobenzone). While chemical sunscreen ingredients tend to offer superior UV shielding effects compared to physical sunscreen ingredients, they have the potential to penetrate the skin, which can lead to irritation and other adverse effects. In contrast, physical agents, though sometimes associated with safety concerns such as skin damage or irritation, are less readily absorbed into the skin.

Antibacterial agents can also be divided into two primary categories, organic and inorganic antibacterial agents. Historically, organic antimicrobial agents have been widely used to combat various microorganisms, with research primarily focused on this category ongoing in many countries. However, in response to growing environmental and health concerns, researchers have identified several drawbacks associated with organic agents. For instance, Triclosan, an organic antibacterial agent commonly found in cosmetics, toothpaste, body wash, and soap, was once present in 75% of antibacterial liquid body washes and soaps in the US, as reported by the FDA. Yet, there is insufficient evidence to substantiate Triclosan's antibacterial efficacy. Further studies have indicated that Triclosan may disrupt growth and reproductive hormones and has been linked to liver cancer and fibrosis by interfering with muscle contraction. As such, attention has gradually shifted towards inorganic antibacterial agents, which have been deemed as safer and more stable alternatives to their organic counterparts. Inorganic NPs can offer numerous advantages when incorporated as antibacterial ingredients in skincare formulations, bolstering skin barrier penetration and stability, as well as providing flexibility for specialized surface modifications and the ability to control size and shape attributes.

As such, understanding the fluid pathways and three-dimensional surface area of the skin architecture is crucial for developing effective topical formulations that can target specific skin needs with optimal cellular uptake and absorption. While non-functionalized fullerenes are large, carbon-based lipophilic structures, and thus relatively soluble in fats and oils, halogenation serves to increase fullerene polarity whereby halogen atoms are more electronegative than carbon, resulting in a more amphiphilic particle compared to an unmodified fullerene. In terms of topical cosmetics and therapeutics, polar molecules generally diffuse deeper into the tissues, while lipophilic particles of 10 nm or less carrying a positive charge can passively permeate through the epidermis to reach the deeper skin layers. While innumerable approaches to aqueous, glycerol and lipid hydration, anti-inflammatory, cleansing and nourishing skincare benefits have been developed and commercialized, the use of NPs has also shown promise as an antioxidant in enhancing skin cell health and neutralizing interstitial pathogens by penetrating deeper layers.

Notably, the ability of NPs to penetrate cells is influenced by a host of their physiochemical characteristics, such as concentration, exposure frequency, the effects of their carrier medium, and the methods used for evaluating their absorption and toxicity. Other factors that impact absorption following dermal application encompass a variety of skin conditions affecting surface integrity, including contact dermatitis, allergies, and psoriasis. Similar consideration should also be given to the route of entry, such as absorption through skin cells, hair follicles, and sebaceous or sweat glands. Furthermore, the loss of applied compositions from the skin surface, whether due to natural skin exfoliation or cleansing, can influence overall absorption. Smaller molecules (sub 600 Da molecular weight) also penetrate human skin quickly; however, fullerenes, which have a molecular weight around 720 Da, diffuse more gradually through the skin, and their polarity allows for continued penetration and activity in more aqueous layers, beyond typical depths for smaller molecules absent NP carriers.

The primary barrier that topical formulations must penetrate is the lipidic and acidic stratum corneum, in contrast to deeper, more aqueous layers of the skin as noted above. Due to their atomic size and unique properties, NPs can readily penetrate the stratum corneum and diffuse into underlying tissues, making these particles particularly useful for topical cosmetic and therapeutic formulations. NP formulations are also being increasingly adopted for use in transdermal drug delivery systems (TDDSs), which leverage these capabilities to optimize drug delivery rates and enable local administration of therapeutics that must traverse the skin barrier, enter the bloodstream, and reach target concentrations. The use of carriers with NPs can thus enhance skin penetration and absorption of macromolecular drugs, as well as reduce their immunogenicity.

While NPs are remarkably stable, skin regeneration is a dynamic and continuous process, constantly creating new cells and shedding expired cells from the surface. This cellular renewal cycle that typically spans 30 days, or keratinization, originates in the stratum basale, whereby keratinocytes underpin this mechanism. As these fresh cells form, they migrate toward the surface, undergoing transformation, flattening and becoming engorged with keratin. This accumulation of keratin is crucial, fortifying the cells as they approach the outermost layer or stratum corneum. Upon reaching the stratum corneum, these keratin-enriched cells form a robust, protective barrier against environmental factors. This cellular procession from the stratum basale to the stratum corneum culminates in the shedding of these surface cells, as new cells migrate outward.

In fact, fullerenes have been employed as atomic-scale, novel allotropes of carbon to provide a robust platform for next-generation skincare nanomaterial innovations, including ultraviolet absorption, antimicrobials, free radical scavengers, wrinkle inhibitors, melanin inhibitors, fillers/extenders and pigmentation materials. Their unique electronic attributes and distinctive spherical cage structure combine with substantial surface area to allow for versatile functionalization, while offering exceptional antioxidant capacities even at low concentrations (Dellinger et al., 2013). The scale, stability and functionality of NPs also enhance penetration, absorbing efficiency, and biological interactions, while their electronic properties and functional abilities can provide antioxidant and antimicrobial activity and ultraviolet protection. Given the harmful impact of oxidative stress and free radical damage on cellular function, the inherent characteristics of fullerenes have thus inspired innovation for utility across biomedical and skincare industries.

The distinctive properties of fullerenes are thus primarily linked to NP electronic activity. Their robust electron reception and unique scavenging abilities are derived from extensive π-bond conjugation with distinct P-orbitals. Their distinct cage-like structure with delocalized π-molecular orbital electrons enables remarkable electron transfer owing to low reorganization energy, low-lying excited states (both singlet and triplet), and prolonged triplet duration. Moreover, the spherical arrangement of planar benzene rings applies an exceptional constraint on the π-electron orbitals. Thus, the carbon cage continuously absorbs and disperses electrons in a regenerative manner. In addition to such free-radical scavenging that can reduce oxidative stress to skin cells, this feature proves lethal to pathogens, as they lack a protective nuclear membrane around their genetic material. While beneficial to human tissues, free electrons orbiting the fullerene cage directly interact with pathogens and, absent nuclear membranes, this oxidative stress damages microbial genetic material and inhibits microorganism proliferation. These properties provide potent antioxidant capabilities that neutralize ROS, as well as reduce pathogen burden.

While fullerenes offer an array of unique advantages in skincare applications, it is important to note that a myriad of alternative NPs and elements have also been combined to enhance the effectiveness of various products. For example, AgNPs exhibit remarkable antibacterial properties, as they target multiple bacterial structures simultaneously, enabling them to eliminate a broad spectrum of microbes.

Zinc Oxide nanoparticles (ZnO NPs) are also of notable significance given their unique chemical and physical attributes with applications established in agriculture, textiles, the rubber industry, biomedicine, and skincare—including as active ingredients in topical sunscreens. The closely matched refractive indices of ZnO NPs and fullerenes significantly improve the transparency of ZnO NPs. These NPs possess antibacterial, UV-blocking, and healing and skin regeneration (following injury) capabilities, high electron mobility, broadband gap, semiconducting behavior, photostability, and biocompatibility. In the United States, the Food and Drug Administration (FDA) has designated ZnO as a Generally Recognized as Safe (GRAS) substance, reinforcing its safety profile for inclusion in cosmetics.

Previous patents and research have described the use of fullerenes in skincare compositions for their therapeutic and cosmetic effects, as well as ultraviolet protection and antimicrobial cleansing.

In Japanese Patent No. 3,506,349B2 entitled, Sun care cosmetic composition, a sun care cosmetic composition containing fullerenes for protection of the skin and hair from ultraviolet (UV) rays is described. The beneficial properties of the sun care composition are derived from pristine fullerenes (0.001 to 1.000 wt % of the overall composition) and a solubilizer. Non-functional fullerenes used in the composition contain 60 carbon atoms ($C_{60}$), or a mix of 60 and 70 carbon atoms ($C_{60}$ and $C_{70}$). The solubilizer or carrier in the described sun care composition is dicarboxylic acid ester oil, or optionally, 2-Ethyl ether and cetyl xanthates. The utility of the composition described in 3,506,349B2 is directed at UV absorption, and/or UV scattering to enhance sun protection.

In contrast, the proposed patent herein teaches the use of halogen-functionalized fullerenes (halo-fullerenes) that impart increased stability and viscosity, promote physiologic electrolyte balance, and offer more robust antimicrobial activity than non-functional counterparts described in 3,506,349B2. In addition, the proposed patent embodiments further encompass the option of impregnating the functional halo-fullerene with specific NPs that introduce robust UV scattering capabilities and have inherently potent antimicrobial properties. The present invention is thus a composition that can synergistically provide superior topical antimicrobial activity and environmental protection, thereby extending its potential utility.

U.S. Pat. No. 5,484,597A entitled, Clear hydroalcoholic cosmetic microemulsions, describes a cosmetic microemulsion composition containing 0.1 to 3.0% fullerenes ($C_{19}$ and $C_{50}$), vitamin oils, or mixtures thereof. The composition is stable when stored and provides quick drying and cooling characteristics, as well as antimicrobial activity. In contrast to 5,484,597A, the proposed patent teaches that halo-fullerenes and halo-endohedral fullerenes provide greater antimicrobial activity and environmental protection compared to native, non-functionalized fullerene constructs.

European Patent No. 2,989,070B1 entitled, Improved fullerene derivatives and related materials, methods and devices, describes a method for enhancing fullerene solubility by increasing the number of solubilizing groups. Additionally, Kraevaya et al. (Org. Biomol. Chem., 2019, 17, 7155) describe an inverse Arbuzov reaction that resulted in halogenated, water-soluble fullerene compounds with halogen functional groups. Other common methods reported to enhance the solubility of fullerenes in an aqueous phase include liposome encapsulation, as detailed in Chinese Patent No. 109,260,035A (Anti-ageing composition of a kind of whitening containing fullerene and preparation method thereof) and Japanese Patent No. 4,834,775B2 (Sunscreen composition).

While this approach provides a seemingly straightforward route to producing an aqueous dispersion of fullerenes, the requisite creation of liposomes involves a complex procedure, and encapsulation can alter material function and activity.

Japanese Patent No. 5,283,102A entitled, Cosmetic composition for make-up, outlines a formulation that includes dispersible fullerenes or fullerene mixtures, serving as extenders/fillers or pigments in a suitable cosmetic vehicle. The composition is designed for use in a range of products, including eyeshadow, eyeliner, mascara, foundation, rouge, blush, coloring cream, lipstick, concealer, and nail enamels. The material comprises between 0.01% to 50% by weight of fullerene nanoparticles, specifically $C_{60}$, $C_{70}$, or $C_{84}$ fullerenes, or a blend thereof. The suitable cosmetic and dispersion vehicles include oil-in-water or water-in-oil emulsions containing surfactants and an oleaginous phase. Other possible formats include fluid, compressed powder, solid, or an anhydrous paste that incorporates a binder. In the case of aqueous nail enamel, the composition is described to include a film-forming substance and resin. The teachings of 5,283,102A speak to a filler or pigment cosmetic material comprising dispersible fullerenes or fullerene mixtures, but they do not disclose the use of functional fullerenes, endohedral fullerenes or more particularly halo-fullerenes and halo-endofullerenes. Likewise, Japanese Patent No. 5,283,102A does not describe or contemplate the use of a cosmetic composition consisting of halogen functional fullerenes nor endohedral fullerenes with antimicrobial and antioxidant properties.

Fullerenes have been shown to protect against DNA damage caused by lipid peroxides in human skin keratinocytes. Previous patents have described creams, emulsions, lotions, and oils comprising fullerenes with other cosmetic ingredients at various concentrations. In PCT/JP2009/053991 entitled, Anti-wrinkle composition and external skin composition, a skin-smoothing composition containing oil-soluble $C_{60}$, $C_{70}$ or a combination thereof is described. The composition described in PCT/JP2009/053991 teaches the induction of double-stranded DNA and/or single-strand breakage, as well as DNA base damage caused by oxidative stress, including lipid peroxide and ROS, in dermal keratinocytes, fibroblasts and tissue. The oil-soluble fullerene composition is designed to inhibit wrinkle formation by mitigating DNA double-strand breaks accompanied by cell membrane damage induced by lipid peroxide nonadienal in human skin keratinocytes. The active NPs of the proposed patent diverge from the pristine fullerenes of PCT/JP2009/053991, by adding halogen side-chain moieties to the fullerene cage and alternatively co-functionalizing the fullerene with halogen and silver NPs (AgNPs) or impregnating the fullerene cage with zinc oxide NPs (ZnO NPs).

Japanese Patent No. JP2008061757A entitled, Fullerene liposolution and its aqueous dispersion as well as antioxidant and cell damage inhibitor, describes a fullerene-fat solution, wherein $C_{60}$ or $C_{70}$ fullerenes (0.00001% to 30% by weight) are suspended in a lipid. The oil-dissolved fullerene composition of JP2008061757A teaches the use of fullerenes as antioxidants in cosmetics and use as cytotoxicity inhibitors for conditions such as UV injury, sunburn, skin lipid metabolism abnormalities, photo-aging and photocarcinogenesis. Similarly, Japanese Patent No. JP2005060380A entitled, Solubilized fullerene composition, describes a cosmetic composition containing fullerenes with active oxygen scavenging ability, anticancer effects, antiviral effects, and antibacterial effects, as well as their efficacy in addressing atopic dermatitis, skin aging, and arteriosclerosis. The solubilized NP of JP2005060380A include $C_{60}$, $C_{70}$, $C_{82}$ and nanotube fullerenes and various functional groups such as amino and organic groups. The active components of the present invention differ in functional moieties, as both JP2005060380A and JP2008061757A are silent with respect to the inclusion of halogen, AgNPs and ZnO NPs as functional elements of the fullerene derivative.

According to U.S. Pat. No. 5,587,168, fine powders of gold (Au) or silver (Ag) are used in consumer preparations that contain gold, silver, or platinum (Pt). The material powder inclusions are directed at making a product more appealing to the consumer. In U.S. Pat. No. 6,720,006, an antimicrobial body care product with a quantity of 1 to 2000 ppm is disclosed. This product is used on a surface with exposure to human or animal skin and/or mucous membranes. The distinguishing feature of 6,720,006 is that a certain quantity of homogeneously dispersed AgNPs with a diameter of 1 to 50 nm are present in an organic matrix. Moreover, the process for generating silver colloids using electrolysis and using such colloids in skincare was disclosed in U.S. Pat. No. 5,932,251A. The tiny particles can nonetheless agglomerate or adsorb on the surface of the container during long-term storage, which often results in discoloration and antibacterial activity. In Korean Patent No. KR101,835,214B1, gold or silver nanoparticles were used to improve the scattering and blocking of UV rays, to minimize the effect of the core material on the skin and sanitize the skin. While the teachings of U.S. Pat. Nos. 5,587,168; 6,720,006; 5,932,251A and KR101,835,214B1 describe metallic NP compositions and applications, the prior art does not speak to fullerenes, halo-fullerene, or co-functional metallic NPs and halogen fullerene.

Another such application is disclosed in Japanese Patent No. JP2000-297005 for a cosmetic formulation that incorporates a zinc oxide powder with suppressor activity. The powder is produced by crushing zinc oxide coated with silane or a silazane compound, which reacts with the inorganic oxide, using a wet-type crusher. The silane or silazane compound utilized in this process possesses a 20-60C alkyl group. In US Patent No. 2004/071956, a polymer composite particle with stability in an A/C emulsion (oil-based and water-based components) is described. The emulsion cosmetic teaches effective UV protection and delivers a distinct sensation upon application. The particle is synthesized through the polymerization of a crosslinking agent and a specific vinyl monomer in specific proportions. Preferably, the particle includes a metal oxide coated with a fluorine and/or silicone compound, with an average particle diameter of ≤1 µm. Similarly, European Patent No. EP0317272A1 entitled, Flaky powder of zinc oxide and its composition for external use, describes ZnO NPs in an average laminar ratio of at least 3 with an average particle thickness of 0.01 to 0.2 µm and a particle diameter range of 0.1 to 1 µm. EP0317272A1 teaches the utility of the ZnO NPs for an external composition that also contains another pharmaceutical or cosmetic ingredient. The art described in teachings of JP2000-297005; 2004/071956 and EP0317272A1 describes metallic oxide NP formulations and applications; however, these filings are silent with respect to fullerenes, halo-fullerene, or halo-endofullerenes with metallic oxide NPs inserted into the fullerene cage.

According to Korean Patent No. KR102089178B1, entitled "Antimicrobial agent containing Ag-Zinc oxide nanocomposites as active component," a method for the creation of an antibacterial nanocomposite is outlined. The described nanocomposite comprises silver and zinc metals that act as photocatalytic antibacterial agents. Constructed from zinc oxide nanoplates on hexagonal plates of 50 to 70 nm in diameter and 10 to 20 nm thickness, in conjunction with silver nanoparticles averaging 5 to 15 nm in diameter, the composition also includes copper particles to provide an antimicrobial with efficacy towards Gram-negative and Gram-positive bacteria. In KR10208917B1, the sizes and concentrations of the nanoparticles contribute to bactericidal properties of the nanocomposite, conferring sterilization under UV irradiation. Whereas the art of KR10208917B1 does not propose halogen functionalized or halo-endofullerenes with metallic oxide NPs inserted into the fullerene cage.

In contrast, the present invention centers on a topical composition employing strategically functionalized fullerenes with halogen side chain moieties, as they can penetrate deeper into the skin layers and leverage the skin's inherent properties and osmotic pathways. In various embodiments, these engineered particles can possess unique characteristics, including atomic-scale activity, enduring electron pairing, antimicrobial capabilities, UV protection and free-radical scavenging abilities. By leveraging the anatomic wobble and orbital space, they can reach vulnerable matter like microbes while remaining inert with respect to skin cells. With targeted engineering, fullerene-based formulations thus have the potential to extend skin cell health and mitochondrial production. Whereas many conventional approaches use absorbent cream formulations with limited penetration, thereby yielding limited cellular benefits despite claims of antioxidant properties and oxidative stress relief.

SUMMARY OF THE INVENTION

The present invention is a multifunctional halo-fullerene-based topical skincare composition with cosmetic and therapeutic applications through delivery of readily absorbed, biofunctional ingredients with: (1) Antimicrobial capabilities associated with NP and functional halogen side chain contact—combined with release of antimicrobial ions—that disrupt pathogen structure and inhibit microbial DNA replication and enzymatic processes without affecting adjacent tissue cells; (2) Inundation of pathogenic DNA with ROS, oxidizing the protein and peroxidizing lipids to destroy pathogens; and (3) Scavenging tissue free-radicals and establishing redox balance to reduce oxidative stress on skin cells. The fusion of deep skin penetration, potent antioxidant activity, antimicrobial and enduring efficacy can thus enhance the appearance as well as the metabolic equilibrium of dermal tissues at the cellular level.

The utility of the present invention is derived from active ingredients that are specific, safe, stable and effective—and can be produced economically. The topical formulation comprises nanoscale, active components combined as a suspension, including but not limited to: (1) halo-fullerenes; (2) endohedral halo-fullerenes; (3) metallic NPs as safe yet potent antibacterials; and (4) metallic oxide NPs with UV-scattering and antibacterial activity.

This invention employs a halogen-functionalized fullerene, wherein the halogen attached to the fullerene could be chlorine, bromine, iodine, or another appropriate halogen compound. The functionalization entails a bonding of the halogen to the carbon cage of the fullerene, ensuring a stable integration rather than an association of proximity. This stable attachment is critical for the fullerene to consistently exhibit its enhanced properties. The caustic characteristics of the halogen-functionalized material on the side chain can effectively neutralize a wide range of microorganisms on contact.

Due to the unique spherical structures of fullerenes, the NPs in the present invention can also demonstrate profound scavenging capacity for unstable atoms (free radicals) and readily neutralize reactive oxygen species (ROS) that can damage cells.

With respect to sunscreen embodiments, the functional fullerene and functional endohederal fullerene metallic-oxide NPs of the present invention are considered non-toxic, safe and physiologically biocompatible. Topical application of low dosage concentrations, below the recommended daily intake (RDI) levels, of the functional fullerene and functional endohedral fullerene can thus penetrate and result in rapid sterilization, enhanced healing, and UV protection.

The compositions described herein possess carbon and halogens, as well as impregnated metallic and metallic oxide NPs, however, the atomic scale mass of the active ingredients enables the material to disrupt microbes, scavenge free-radicals, and target delivery of specific additives while maintaining dermal homeostasis. For example, silver nanoparticles (AgNPs) are considered safe for humans and have long been used as a generic antibiotic across a variety of disciplines. The US Food and Drug Administration (FDA) does not classify silver electrolysis solutions as medicines because they are currently accepted as natural chemicals. AgNPs antimicrobial activity is directly correlated to surface contact, and very small, stable and well dispersed particles have shown exceptional antimicrobial effects against over 650 pathogenic bacteria and fungi.

The proposed invention comprises functionalized fullerenes with coordinated bonding of halogens and NPs that is achieved through a rapid, one-step synthesis. In the context of this invention, coordination chemistry is utilized to describe the formation of complexes between metal ions and ligands. Ligands are molecules that donate pairs of electrons to establish coordinate covalent bonds with metal ions. This interaction leads to the creation of stable complexes where the metal ion is centrally positioned, surrounded by an array of ligands that are bonded through shared electron pairs. The coordinate bond, however, arises not through the sharing of one electron from each of two partner atoms, as occurs in a standard covalent bond; but rather, it forms through the donation of a pair of electrons from an orbital on one atom (fullerenes) to occupy an empty orbital in its partner atom (silver or zinc ions). The coordination results in chemical binding of silver to the exterior of the fullerene structure, altering the electronic charge distribution across the molecule.

This modification results in a unique charge polarity, with positive ends attributed to the silver ions, while the core fullerene cage maintains a net negative charge. Unlike physical attachment methods, chemical binding (i.e., formation of covalent or ionic bonds) lead to changes in molecular vibrational modes, including stretching vibrations. Whereas physical attachment, which typically involves weaker interactions (i.e., van der Waals forces or hydrogen bonding) would not result in significant changes in vibrational modes. Thus, altering the vibrational modes of the fullerene molecules, and impacting specific carbon atom stretching, enable precise control over the number of bound silver, zinc or both atoms and their interactions in the halo-fullerene-NP complexes.

This proposed invention can thus establish a new class of topical cosmetic and therapeutic compositions that harness inert and functionalized particles with exceptional penetration capabilities and the ability to cleanse interstitial pathways. The safe and inert characteristics of the proposed nanomaterial ingredients support their use as innovative components in the cosmetics industry with potential utility as topical therapeutics.

DETAILED DESCRIPTION OF THE INVENTION

Figure 1:
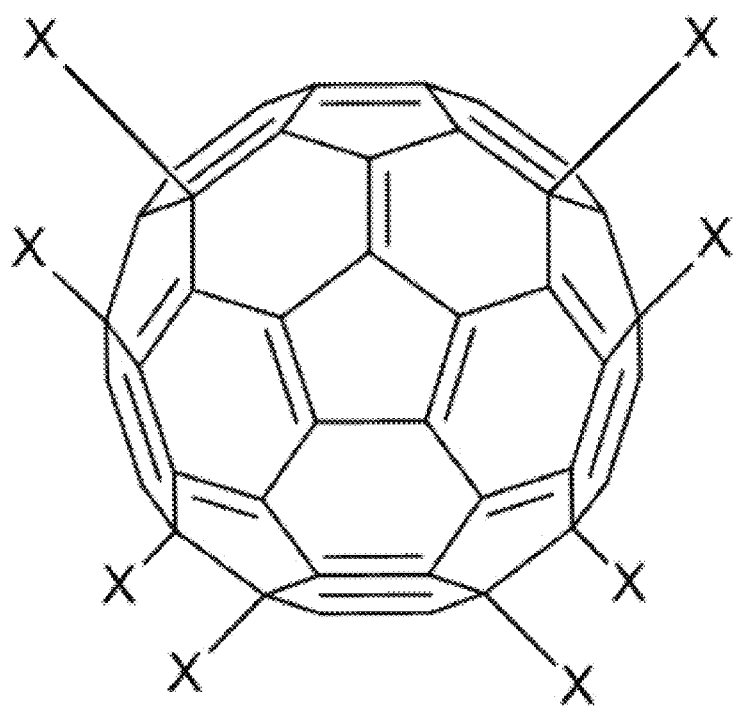
FIG. 1 is a molecular representation of an exemplary halo-fullerene of 60 carbons functionalized with halogens (X).
Figure 2:
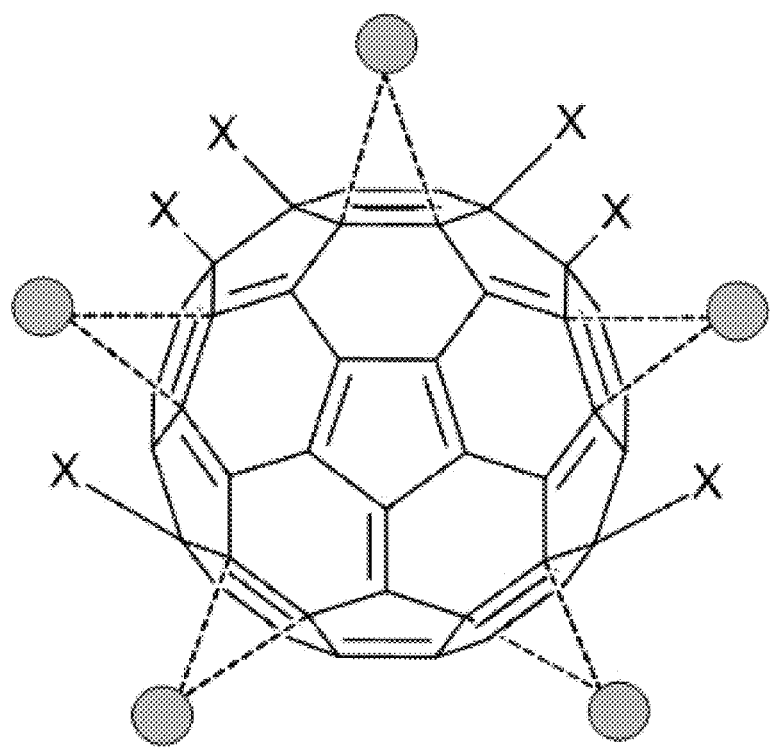
FIG. 2 is a molecular representation of an exemplary halo-fullerene of 60 carbons functionalized with halogens (X) and anti-bacterial NPs (i.e., AgNPs; gray circle) that are coordinated to the outside the fullerene cage.
Figure 3:
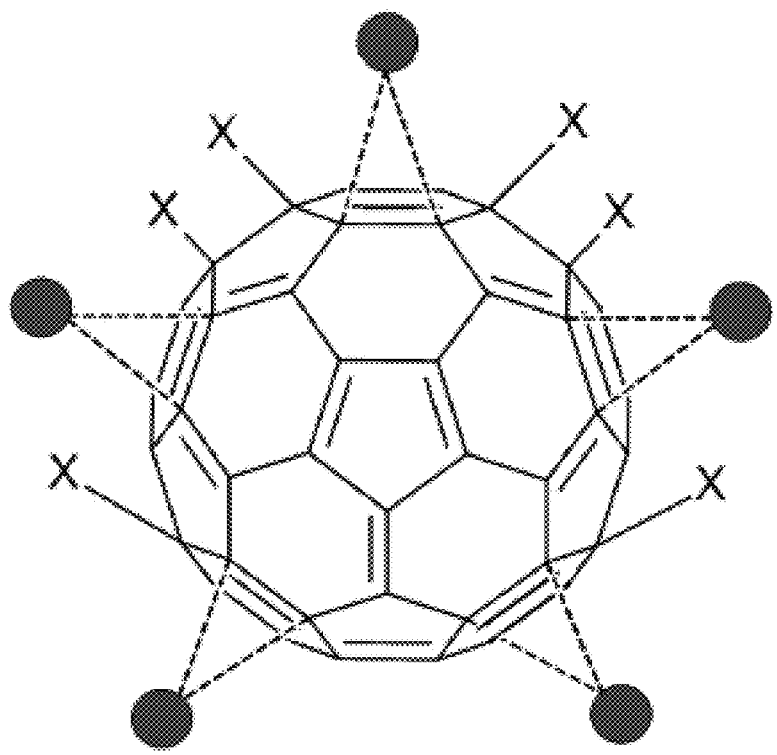
FIG. 3 is a molecular representation of an exemplary halo-fullerene of 60 carbons functionalized with halogens (X) and UV-blocking NPs (i.e., ZnO NPs; black circle) coordinated outside the fullerene cage.
Figure 4:
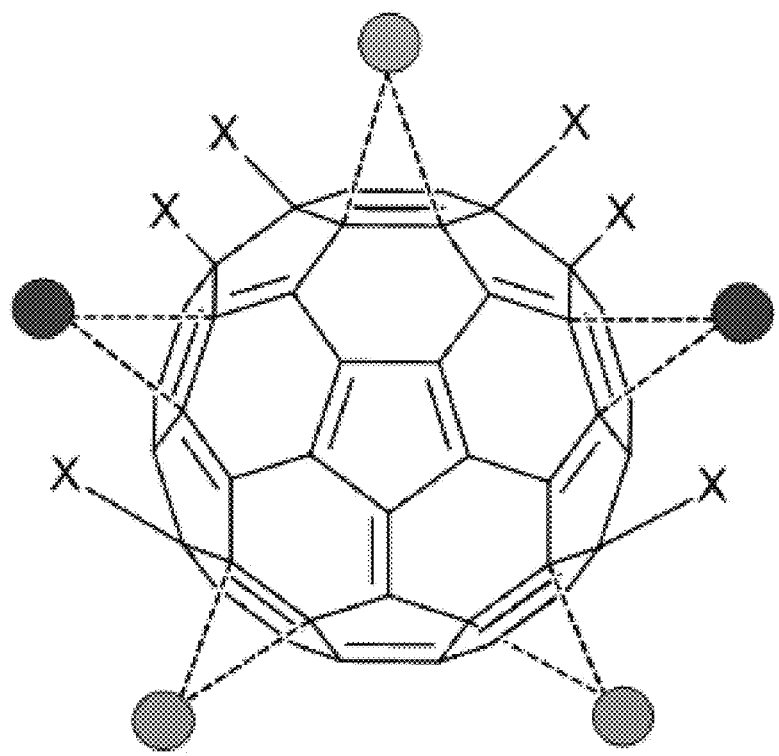
FIG. 4 is a molecular representation of an exemplary halo-fullerene of 60 carbons functionalized with halogens (X) and containing anti-bacterial NPs (i.e., AgNPs; gray circle) and UV-blocking NPs (i.e., ZnO NPs; black circle) coordinated outside the fullerene cage.

The object of this invention is to create a composition using functionalized fullerenes and NPs in a stable form for use as a topical skin protectant/moisturizer, antioxidant, therapeutic and broad-spectrum antimicrobial. This innovation combines halogen-functionalized fullerenes (halo-fullerenes) and halogen-functionalized endohedral fullerenes (halo-endofullerenes) enriched with silver nanoparticles (AgNPs), zinc oxide nanoparticles (ZnO NPs), or combinations thereof. In the present invention, the fullerene functions as a platform, whereby the external cage can be chemically altered to achieve different functionalities, depending on specific performance objectives to enhance the biochemical interactions with skin, thereby enhancing cellular hydration, mitigating microbial activity, scavenging free radicals and providing protection from UV and other harmful radiation.

A primary embodiment of the present invention comprises halo-fullerenes, halo-endofullerenes and optionally functional silver (Ag) and zinc oxide (ZnO) NPs capable of penetrating the skin barrier. This permeable membrane has characteristic, semi-circular channels that vary in diameter from 0.4 nm to 36.0 nm. The atomic-scale NPs can readily deliver active ingredients through the skin via the pores of sweat glands, with diameters ranging from 60-80 μm; the lipid matrix of the stratum corneum; and hair follicles, sebaceous glands, and pilosebaceous pores, which possess a diameter of 10-70 μm. Topical delivery of the composition can thus traverse the skin via the trans-follicular pathway, which employs skin appendages, or through the intercellular and intracellular channels within the stratum corneum.

A second embodiment of the present invention comprises: halo-fullerenes, a delivery vehicle and optionally a penetration enhancer, cosmetic, nutritive, or therapeutically active ingredient(s) and water. Wherein the halo-fullerene represents a fullerene of $C_{2n}$, whereby n=10, 12, 13, 14, 15, . . . , 360, that contains multiple side-chain halogens attached to the carbon cage. As shown in FIG. 1, an exemplary molecule of the present invention relates to the $C_{60}$ fullerene functionalized with eight halogen molecules. In alternative embodiments, the halo-fullerene may comprise the three typical functionalization patterns including: $C_{60}X_6$, $C_{60}X_8$ (FIG. 1), and $C_{60}X_{24}$; whereby X=a halogen molecule (e.g., iodine, bromine, chlorine or fluorine); whereas the composition may also comprise halo-fullerenes further modified with antimicrobial NPs (FIG. 2) on the exterior of the cage structure, such as metallic NPs (e.g., AgNPs). The halo-fullerene possesses an inherent molecular affinity for pathogenic species, augmented by the introduction of broad-spectrum antimicrobial halogens, which are capable of prolonged microbial neutralization.

In FIG. 2 a molecular representation of an exemplary halo-fullerene comprised of a 60-carbon atom sphere is depicted, wherein each carbon atom is denoted as a vertex on the geometric structure. The fullerene is functionalized with halogens, represented by the symbol "X"; these halogens are covalently bonded to the carbon cage at designated positions. Additionally depicted are anti-bacterial nanoparticles (NPs), indicated by gray circles, which are AgNPs (silver nanoparticles). These nanoparticles are coordinated to the fullerene cage, and quantified to form a stable complex wherein the silver atoms engage in directional bonding with specific carbon atoms on the fullerene cage surface.

FIG. 3 shows a molecular representation of an exemplary halo-fullerene consisting of a 60-carbon atom framework. Herein, the halogens symbolized as "X" are functionalized on the carbon structure. UV-blocking nanoparticles, indicated by black circles, which are ZnO NPs (zinc oxide nanoparticles), are coordinated outside the fullerene cage. This coordination implies a stable interaction between the ZnO NPs and the carbon cage with a quantified number of the NPs, facilitating the fullerene's ability to block ultraviolet radiation, thereby enhancing its potential use in photoprotective applications.

FIG. 4 illustrates a molecular representation of another exemplary halo-fullerene with 60 carbon atoms forming the spherical structure, functionalized with halogens marked as "X." This fullerene shows dual functionalization, whereby the carbon cage of the fullerene is simultaneously coordinated with anti-bacterial AgNPs, displayed as gray circles, and UV-blocking ZnO NPs, shown as black circles. The nanoparticles are positioned outside the fullerene cage and bound through coordination chemistry. The presence of a quantified number of both AgNPs and ZnO NPs on the fullerene imparts it with multiple properties for antimicrobial efficacy and ultraviolet radiation blocking, respectively.

This invention presents a composition resulting from chemical functionalization of fullerenes with chlorine and the coordination of AgNPs and/or ZnNPs attached to the external surface of the fullerene cages using a one-step process. The invention indicates that the silver nanoparticles are attached to the cage rather than simply juxtaposed due to forces during the mixing process. This attachment results in a notable alteration of the overall charge distribution within the fullerene molecule, distinct from a mere physical association.

In this embodiment, the addition of nutritive agents can leverage the extended dermal cellular life cycle to deliver enhanced interstitial benefits. While nutritive agents enhance cellular formation and growth, the halo-fullerenes combine surface and interstitial antimicrobial activity with reduced exposure to toxins and radiation, leading to overall improved skin health and appearance. These properties can help to maintain appropriate moisture levels throughout keratinization, creating a visibly smooth complexion via improved cellular integrity.

In addition to antimicrobial activity in the present invention, the halo-fullerenes harness unique capabilities as scavengers of free radicals and neutralize the damaging effects of ROS that cause oxidative stress, cellular degradation, premature skin aging, and a host of skin disorders. The atomic scale of the halo-fullerenes also enables exceptional penetration through complex skin architecture to deliver antioxidant effects deep into epidermal layers, where they can have the greatest benefits through earlier introduction in cell flattening and dermal layering cycles.

Ultimately, as the halo-fullerenes perform deep in the epidermis throughout its 30-day cellular cycle, the particles will be pushed outward and shed as atomic dust with expired skin cells.

The utility of the present invention is derived in part from the distinctive structure of the fullerene that confers unparalleled stability to this molecule. The carbon cage forms an electron reservoir, which not only scavenges but also releases electrons as needed. This allows for continuous free radical scavenging and ROS-neutralizing performance for sustained defense against oxidative stress and pathogenic material. The stability of this halo-fullerene also affords consistent antimicrobial activity as a key component of the present invention.

In a third embodiment of the present invention, the composition may comprise endohedral halo-fullerenes with UV blocking NPs inside of the cage structure (FIG. 3). The process of loading fullerenes with metallic NPs requires attention to both the size of the fullerenes and that of the metallic nanoparticles. Encapsulation of the metallic NPs of the present invention is accomplished via chemical reduction or sonication. In the chemical reduction method, fullerenes are introduced into a recently synthesized solution of metallic NPs. This solution contains a suitable reducing agent, which facilitates the incorporation of metallic NPs into the fullerenes. Alternatively, as implied, the sonication method employs sonication of fullerenes, giving rise to cavitation bubbles to induce high pressure and temperatures that lead to formation of transient hotspots to permit loading of metallic NPs into the fullerenes. Knowhow for optimization of reaction conditions, such as concentration of reagents, temperature, pressure, and reaction time is imperative to ensure successful NP encapsulation and integration into the fullerene.

In a fourth embodiment of the present invention, the composition may comprise a halo-endofullerene chemically functionalized with antimicrobial NPs attached to the exterior of the cage structure with UV blocking NPs inside the cage structure (FIG. 4). In another aspect of the present invention, the composition may comprise a combination of the functional fullerene and endohedreal fullerenes as previously described.

The incorporation of penetration enhancers into a topical composition is common in the skincare industry. Their inclusion can enhance the delivery of active ingredients, particularly in NP-based compositions, by employing a combination of mechanisms. These include but are not limited to altering the lipid structure of the stratum corneum, enhancing solubilization, and reducing surface tension, which in the present invention would facilitate deeper uptake and absorption of halo-fullerenes and NPs, thereby improving the overall effectiveness of the formulation. Other penetration enhancers are often used in anti-aging products or treatments for specific skin concerns to alter the barrier function of the skin, allowing active ingredients to penetrate more deeply. It would be obvious to one skilled in the art that an acceptable penetration enhancer at a safe concentration would increase NP absorption. An exemplary list of penetration enhancers is described below, claimed in various embodiments and may be utilized separately or in combination to achieve desired penetration characteristics in the final product:

1) Dimethyl Sulfoxide (DMSO): Used in skin creams and serums to enhance penetration by creating spaces between skin cells, allowing other ingredients to sink deeper.
2) Ethanol: Used in toners, aftershaves, and perfumes to temporarily disrupt the skin barrier and allow active ingredients to penetrate more rapidly.
3) Glycerol: Used in lotions, creams, and soaps to act as a humectant that facilitates the penetration of substances into the skin.
4) Hyaluronic Acid: Used in serum, moisturizers, and anti-aging products to function as a humectant that binds water to the skin, helping active ingredients penetrate more effectively.
5) Lecithin: Used in creams, lotions, and lipsticks to help to reduce surface tension and allow better mixing and absorption of active substances.
6) Menthol: Used in shampoos, conditioners, and balms to enhance penetration via increasing blood flow to the site of application.
7) Oleic Acid: Used in creams and lotions and comprises a fatty acid that increases the fluidity of cell membranes to enable better absorption of active compounds.
8) Polysorbates: Used in cleansers, emulsifiers in creams and lotions to act as a surfactant that reduces surface tension and aids in the dispersion and absorption of active compounds.
9) Propylene Glycol: Used in moisturizers, sunscreens, and makeup products to act as a humectant and increases absorption of active ingredients.
10) Sorbitol: Used in toothpaste, mouthwash, and anti-aging skincare composition to act as a humectant that draws water into the skin and enhances absorption of active ingredients.

Topical delivery vehicles and solutions for halo-fullerenes and NP-based cosmetics are diverse and can be tailored to various skin types, conditions, and application sites. Each formulation offers unique characteristics including texture, appearance, absorption rate, and moisturizing properties. In the present invention, the selection of the appropriate vehicle or solution is determined by the desired release profile, target skin area, and consumer or patient preferences. An exemplary list of delivery vehicles or solutions for the proposed halo-fullerene and NP-based composition is described below and may be employed individually or in combination to attain the intended performance and effects of a given topical embodiment:

1) Aerosol Foam Formulation: A foam formulation typically comprises a propellant, emulsifiers, and stabilizers. Aerosol foam formulations can provide unique textures, increased solubility, and allow for uniform application of active ingredients over large skin regions.
2) Cream Formulation: A cream-based formulation is especially suited for application on dry or damaged skin. Cream formulations are thick emulsions that typically consist of oils and waxes. This vehicle can create a barrier that may help slow the release of active ingredients for prolonged action at the site of administration.
3) Gel Formulation: A gel-based formulation is a semi-solid composition consisting of dispersions of small or large molecules in an aqueous liquid phase and thickened with gelling agents, such as carbomer or hydroxyethyl cellulose. Gel formulations are usually transparent, non-greasy and allow for rapid absorption of active components.
4) Hydrogel Formulation: A hydrogel-based formulation is comprised of a three-dimensional network of hydrophilic polymers. Hydrogel formulations can bind a significant amount of water, enhance hydration at the site of application, and allow for controlled and sustained delivery of active ingredients.
5) Liposomal Formulation: A liposomal formulation is comprised of spherical vesicles made of phospholipid bilayers that can encapsulate and protect active ingredients, facilitating targeted and controlled release. Liposomal formulations enhance the stability and bioavailability of the active ingredient.
6) Lotion Formulation: A lotion-based vehicle typically provides a lightweight and non-greasy application, suitable for all skin types. Lotion formulations typically consist of an emulsion of oils and water and optionally the inclusion of stabilizers, emulsifying agents, and viscosity modifiers to allow for even dispersion of active ingredients.
7) Micellar Solution: A micellar-based solution comprises surfactants that can encapsulate active ingredients within their micelle structure. Micellar solution vehicles provide gentle and effective delivery and are particularly beneficial for sensitive skin applications.
8) Nano-emulsion Formulation: A nano-emulsion formulation is a stabilized emulsion comprising nano sized droplets that function to enhance surface area and allow for improved dissolution and penetration of active ingredients.
9) Ointment Formulation: An ointment formulation provides a moisture barrier and facilitates prolonged release of active ingredients at the site of application. These anhydrous formulations are rich in lipids and waxes and ideal for applying to dry or compromised skin.
10) Serum Formulation: A serum-based formulation is a typically lightweight, fast-absorbing vehicle designed to deliver more concentrated active ingredients directly to the site of application, compared to cream and lotion-based vehicles.

The described penetration enhancers and delivery vehicles for the application of a halo-fullerene and halo-endofullerene, with or without metallic and metallic oxide chemically functionalized side chain groups or encapsulated moieties, is deemed illustrative, expansive, and non-restrictive. The description provides an adaptable framework to facilitate the controlled release, dispersion, stability, and safety of the active ingredients within various cosmetic or therapeutic formulations. The integration of other or additional ingredients commonly employed within the cosmetics or alternatively, the pharmaceuticals industry, may be judiciously selected, with specific considerations as to physicochemical compatibility with the halo-fullerene structure, optimal efficacy in promoting deeper skin penetration, and adherence to relevant safety standards and regulatory guidelines. The precise composition may be tailored to align with the targeted therapeutic or aesthetic goals, and to conform to the quality and performance requirements pertinent to the intended consumer or therapeutic application. Such materials would include the use of pH adjustors, thickening agents, film formers, gelling agents, preservatives, surfactants, humectants, foaming agents, aerosolizing agents, emulsifiers, emollients, and fragrances common to cosmetics or pharmaceuticals industries.

The proposed topical embodiments leverage the antimicrobial, antioxidant, UV blocking and penetration capabilities of halo-fullerenes and halo-endofullerenes with and without metallic and metallic oxide chemically functionalized side chain groups or encapsulated moieties. As referenced for therapeutic applications herein, it would be obvious to one skilled in the art that the composition presents a multitude of potential applications beyond cosmetics. By example, the deep penetration and persistent antimicrobial activity of halo-fullerenes could facilitate faster, cleaner wound healing by eliminating pathogenic species within the wound and thereby mitigate infection risk. Moreover, the oxidative stress relief afforded by the free-radical scavenging capability of halo-fullerenes could promote the proliferation and differentiation of cells crucial for tissue regeneration and wound closure. Similarly, halo-fullerenes could be incorporated in therapeutics following chemical peels or laser resurfacing. The soothing, hydrating, and antimicrobial properties of the formulation could help expedite healing while reducing the risk of complications.

The antioxidant and radical scavenging properties of the halo-fullerene composition would also be beneficial for mitigating the symptoms of chronic inflammatory skin conditions such as psoriasis or eczema. The targeted, deep-layer action of halo-fullerenes could provide relief by reducing inflammatory oxidative stress and enhancing dermal integrity. Additionally, UV protective properties provided by the AgNPs and ZnO NPs in the cosmetic composition would be useful as a potent, lasting sunscreen, providing superior skin protection against harmful UV radiation. This could reduce the risk of premature skin aging and skin cancers associated with UV damage. Its potential as a sunscreen is enhanced by the fact that the halo-fullerenes can remain active for extended periods until gradually shed from the surface with expired cells, providing prolonged sun protection from deeper penetration.

What is claimed:

1. A topical composition comprising:
   (a) an active ingredient comprising halo-fullerenes coordinated to silver nanoparticles, and
   (b) a delivery vehicle.

2. The topical composition of claim 1, which is for application to the skin.

3. The topical composition of claim 1, wherein the delivery vehicle is selected from the group consisting of a lotion, a cream, a gel, a hydrogel, a serum, a micellar-based formulation, a nano-emulsion, a liposomal formulation, an ointment, an aerosolized spray, and an aerosolized foam.

4. The topical composition of claim 1, wherein the delivery vehicle comprises one or more bases, penetration enhancers, pH adjusters, thickening agents, film formers, gelling agents, preservatives, surfactants, humectants, foaming agents, aerosolizing agents, emulsifiers, emollients and fragrances.

5. The topical composition of claim 1, wherein, when the composition is applied to skin, it provides antimicrobial activity at the application site on the skin.

6. The topical composition of claim 1, wherein halo-fullerenes coordinated to silver nanoparticles have been made from halo-fullerene having the chemical structure $C_nX_m$, wherein n is an integer from 60 to 84; X is a halogen selected from the group consisting of fluorine, chlorine, bromine, and iodine; m is an integer representing the number of halogen atoms.

7. The topical composition of claim 1, wherein the silver nanoparticles-coordinated halo-fullerene has the chemical structure $C_nX_mAg_y$, wherein n is an integer from 60 to 84; X is halogen selected from the group consisting of fluorine, chlorine, bromine, and iodine; m is an integer representing the number of halogen atoms; Ag is a silver nanoparticle; and y is an integer representing the number of silver nanoparticles.

8. The topical composition of claim 1, further comprising zinc oxide nanoparticles.

9. The topical composition of claim 8, which provides antimicrobial activity, antioxidant properties and UV radiation protection at the application site on the skin.

10. The topical composition of claim 1, wherein the active ingredient provides antimicrobial activity at the application site on the skin, and wherein the composition is a dermal sanitizer.

* * * * *